(12) United States Patent
Goldberg et al.

(10) Patent No.: US 11,846,592 B2
(45) Date of Patent: Dec. 19, 2023

(54) SYSTEMS AND METHODS FOR X-RAY COMPUTED TOMOGRAPHY

(71) Applicant: Orimtech Ltd., Buffalo Grove, IL (US)

(72) Inventors: Boris S. Goldberg, Buffalo Grove, IL (US); Serguei Gouzeev, Discovery Bay, CA (US); Michael G. Hellmann, Mount Sinai, NY (US); David R. Zavagno, Solon, OH (US)

(73) Assignee: Orimtech Ltd., Buffalo Grove, IL (US)

( * ) Notice: Subject to any disclaimer, the term of this patent is extended or adjusted under 35 U.S.C. 154(b) by 0 days.

(21) Appl. No.: 17/381,608

(22) Filed: Jul. 21, 2021

(65) Prior Publication Data

US 2022/0011244 A1 Jan. 13, 2022

Related U.S. Application Data

(62) Division of application No. 16/460,936, filed on Jul. 2, 2019, now Pat. No. 11,099,140.

(60) Provisional application No. 62/716,160, filed on Aug. 8, 2018, provisional application No. 62/693,382, filed on Jul. 2, 2018.

(51) Int. Cl.
| | |
|---|---|
| *A61N 5/10* | (2006.01) |
| *G01N 23/046* | (2018.01) |
| *G06T 11/00* | (2006.01) |
| *G01N 23/083* | (2018.01) |
| *G01N 33/24* | (2006.01) |

(52) U.S. Cl.
CPC ......... *G01N 23/046* (2013.01); *G01N 23/083* (2013.01); *G01N 33/24* (2013.01); *G06T 11/005* (2013.01); *G06T 11/006* (2013.01); *G01N 2223/3303* (2013.01); *G01N 2223/419* (2013.01); *G01N 2223/616* (2013.01)

(58) Field of Classification Search
CPC ..... A61B 6/032; A61B 6/4441; A61B 6/4452; A61B 6/4435; A61B 6/4014; A61B 6/025; A61B 6/4458; A61B 6/4464; A61B 6/4405; A61B 6/035; A61B 6/102; A61B 5/0035; A61B 34/30; A61B 90/36; A61B 2090/3762; A61B 2090/367
See application file for complete search history.

(56) References Cited

U.S. PATENT DOCUMENTS

2008/0118035 A1* 5/2008 Maschke .............. A61B 6/4441
378/197

* cited by examiner

*Primary Examiner* — Don K Wong
(74) *Attorney, Agent, or Firm* — Bishop, Diehl & Lee, Ltd.

(57) ABSTRACT

A system and method for X-ray computed tomography includes a robotic arm that moves an X-ray emitter around a subject in a curvilinear path and an X-ray detector that captures 2-dimensional views while the subject is scanned. Movements of the emitter and detector are coordinated such that the position and angle of the emitter relative to the detector remains substantially constant during scanning. A processor uses computed tomography to reconstruct an image of the subject from the captured 2-dimensional views. The robotic arm varies the pitch of the X-ray emitter during the scan to enhance the spatial resolution of the reconstructed image. The processor generates a projection transformation matrix based on movement of the robotic arm for each captured 2-dimensional view that is applied during reconstruction.

9 Claims, 17 Drawing Sheets though some instances of "software" may not include executable code, for example machine-executable or machine-interpretable instructions, but also data structures, data stores and computing instructions stored in any suitable electronic format,

SYSTEMS AND METHODS FOR X-RAY COMPUTED TOMOGRAPHY

CROSS-REFERENCE TO RELATED APPLICATIONS

This application claims the benefit of U.S. Non-Provisional Ser. No. 16/460,936, filed Jul. 2, 2019, which claims the benefit of U.S. Provisional No. 62/693,382, filed Jul. 2, 2018, and also claims the benefit of U.S. Provisional No. 62/716,160, filed Aug. 8, 2018, each which is herein incorporated by reference in its entirety.

TECHNICAL FIELD

The subject application generally relates to computed tomography and, more specifically, to systems and methods of reducing computed tomography artifacts, compensating for movement of a subject during a computed tomography scan, and imaging core samples.

BACKGROUND

Computed tomography (CT) uses an X-ray source and a corresponding X-ray detector to scan an object from a number of different positions or angles. During CT reconstruction, a computing system performs data processing algorithms on data from the X-ray detector from the scans to reconstruct a 3-dimensional representation of the scanned object.

Core drills extract cylindrical samples of sediment and rock from the ground for analysis. By analyzing extracted core samples, companies can make informed decisions about where to drill for oil, gas, or other substances. One method of analyzing core samples is to retain the core samples in metal sleeves and attach high temperature, high pressure lines to the bottom and top of the metal sleeves to determine properties of the core samples such as capillary pressure, density, immiscibility, and so forth. Soaps, alcohols, or liquid $CO_2$ can be introduced to determine how best to extract substances from the ground associated with the core samples. Core samples are typically monitored over a period of time, which can span days or weeks.

CT scanning of core samples allows for non-invasive and non-destructive analysis of the different layers of each core sample. During CT reconstruction, a computing system performs data processing algorithms on data from the X-ray detector from the scans to reconstruct a 3-dimensional representation of the core sample.

However, accommodating core samples in traditional CT scanning apparatuses presents logistical challenges. Core samples are generally very heavy, making it difficult to move core samples into position for scanning by a traditional CT scanner. Moreover, cores are typically mounted inside of a metal sleeve, often with a rubber liner which can allow the cores to move when repositioned. Further complicating movement of the core samples is accommodating the high temperature, high pressure lines that are typically present during testing.

BRIEF DESCRIPTION OF THE DRAWINGS

Various embodiments will become better understood with regard to the following description, appended claims, and accompanying drawings.

DETAILED DESCRIPTION

Figure 1A:
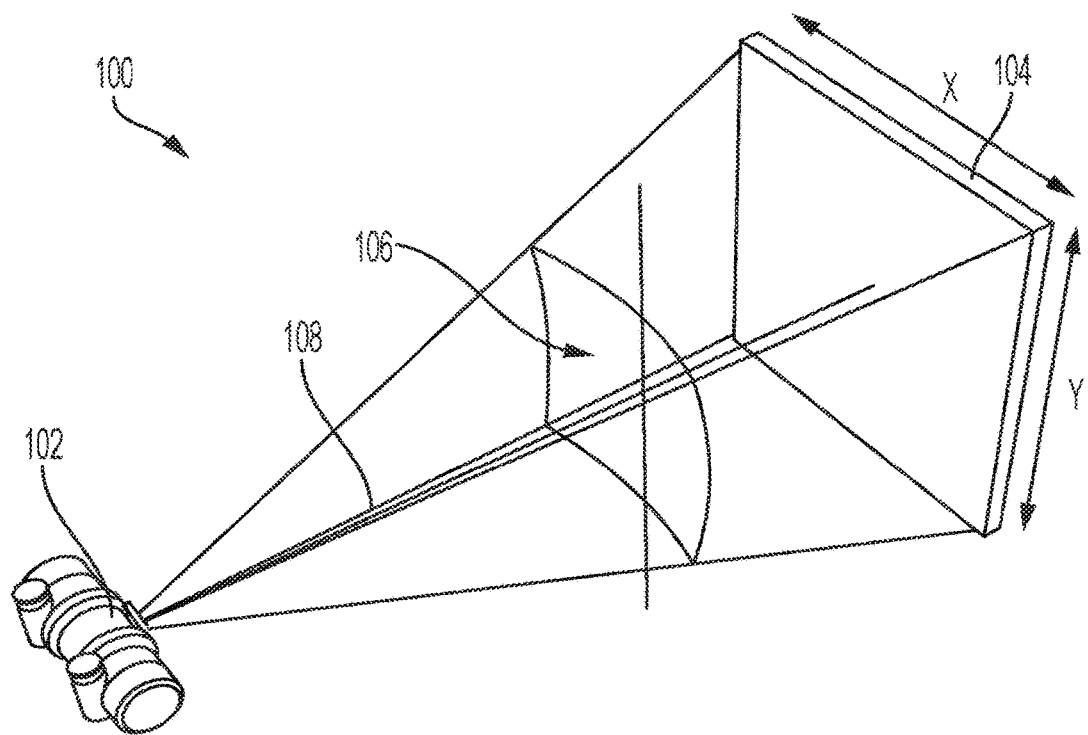
FIG. 1A depicts an example setup for performing cone beam scans.

The systems and methods disclosed herein are described in detail by way of examples and with reference to FIGS. 1 to 14. It will be appreciated that modifications to disclosed and described examples, arrangements, configurations, components, elements, apparatuses, devices methods, systems, etc. can suitably be made and may be desired for a specific application. In this disclosure, any identification of specific techniques, arrangements, etc. are either related to a specific example presented or are merely a general description of such a technique, arrangement, etc. Identifications of specific details or examples are not intended to be, and should not be, construed as mandatory or limiting unless specifically designated as such.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware. The term "software" is used expansively to include not only executable code, for example machine-executable or machine-interpretable instructions, but also data structures, data stores and computing instructions stored in any suitable electronic format, including firmware, and embedded software. It should be noted that although for clarity and to aid in understanding some examples discussed herein might describe specific features or functions as part of a specific component or module, or as occurring at a specific layer of a computing device (for example, a hardware layer, operating system layer, or application layer), those features or functions may be implemented as part of a different component or module or operated at a different layer of a communication protocol stack.

The systems and methods disclosed herein describe improvements to the field of computed tomography that are particularly applicable to scanning and imaging core samples. The systems and methods do not rely on a priori calibration of specific material types, core diameters or core holders and are therefore adaptable to any range of computed tomography configurations for scanning and imaging core samples. However, the systems and methods presented are also adaptable to other suitable computed tomography configurations outside of sampling and imaging core samples.

Figure 1B:
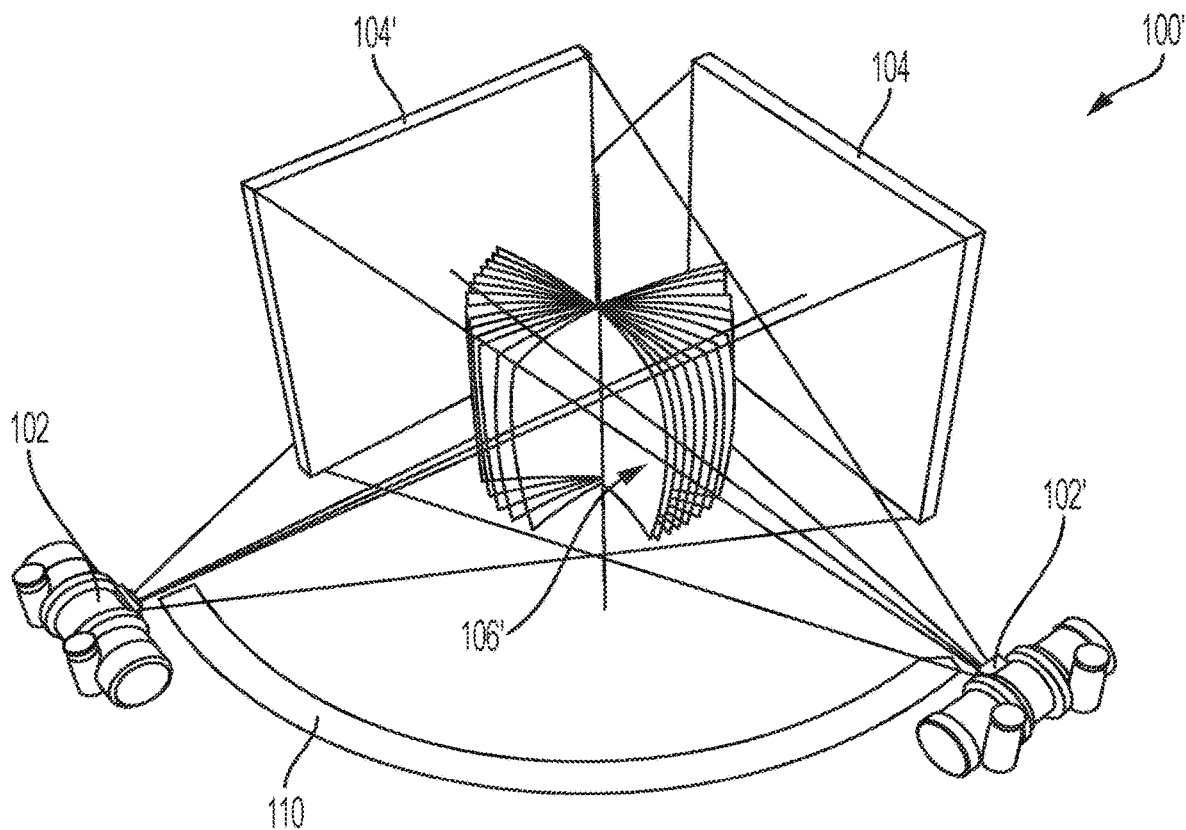
FIG. 1B depicts rotating the cone beam scan of FIG. 1A in an arc to generate a plurality of surfaces.

Referring now to FIG. 1A, a setup for an example cone beam scan 100 is presented. The setup for the cone beam scan 100 includes an X-ray emitter 102 and an X-ray detector 104. X-rays 108 from the X-ray emitter 102 pass through an object and are detected by the X-ray detector 104, represented here as an array of X-by-Y pixels. According to Radon's theorem, a set of one-dimensional Fourier spectra correspond to the surface 106 in a 3D cloud of values representing a Fourier transform of the scanned object. Referring also to FIG. 1B, the cone beam scan 100' is illustrated where the X-ray emitter 102' and the X-ray detector 104' are rotated around the subject in an arc 110 to generate additional surfaces 106'. Each projection contributes to the Fourier spectrum.

Figure 1C:
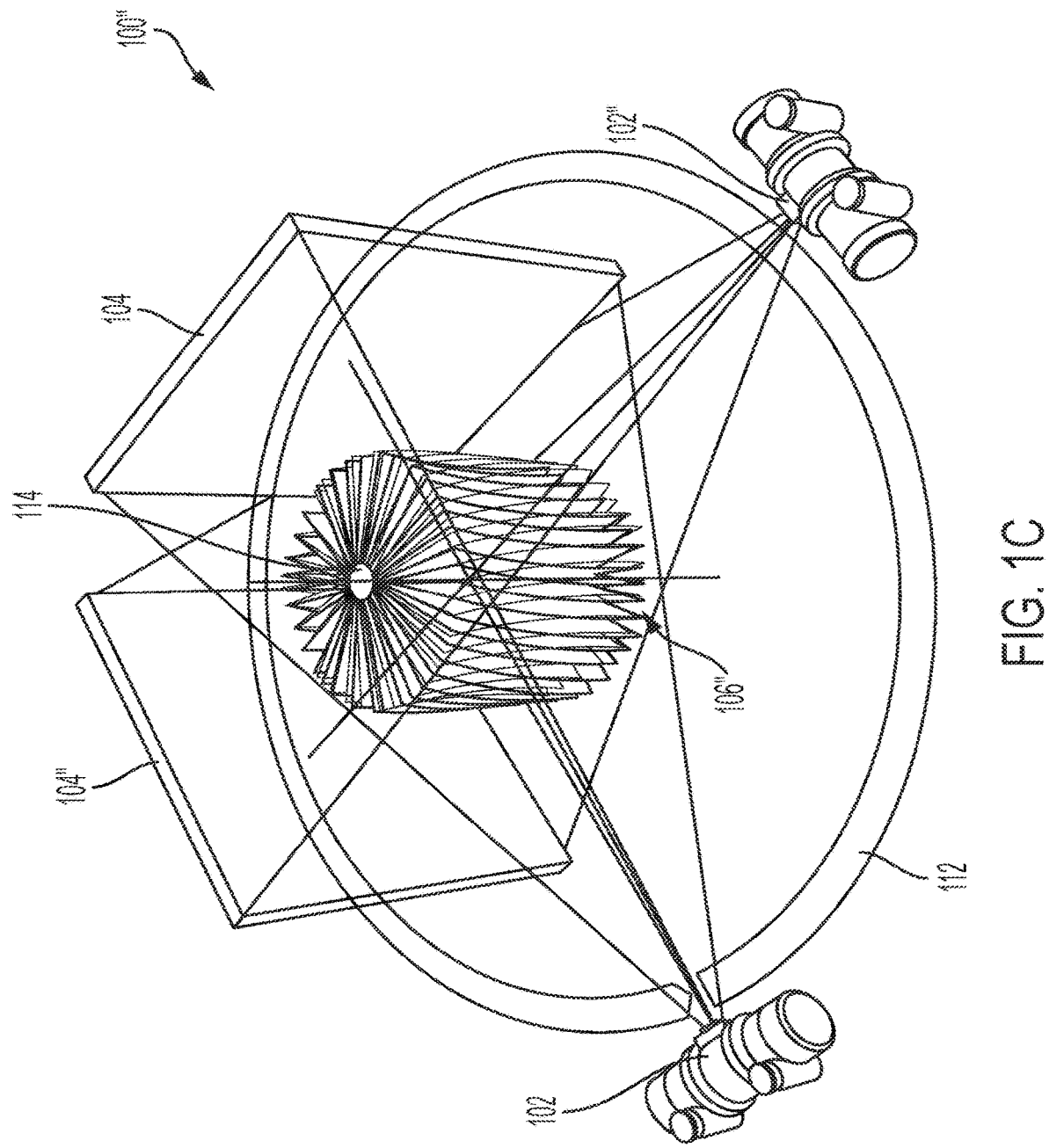
FIG. 1C depicts rotating the cone beam scan of FIG. 1A in a circle to produce a set of surfaces.

Referring now also to FIG. 1C, the cone beam scan 100" completes a full rotation in a circle 112 about the scanned object to produce a set of surfaces 106". However, this circular scan is non-optimal with respect to the accuracy of the calculated density map for the computed 3D CT image. Even if the acquisition process is ideal (e.g., monochromatic spectrum, no scatter distortions, and the X-ray detector has ideal linear sensitivity) reconstruction methods can only produce an insufficient approximation. After all projections have contributed to the Fourier spectrum, there is an area 114 in the spectrum that is not defined. This area 114 is shaped as two funnels located at the "north and south poles" of the spectrum respectively.

Figure 2:
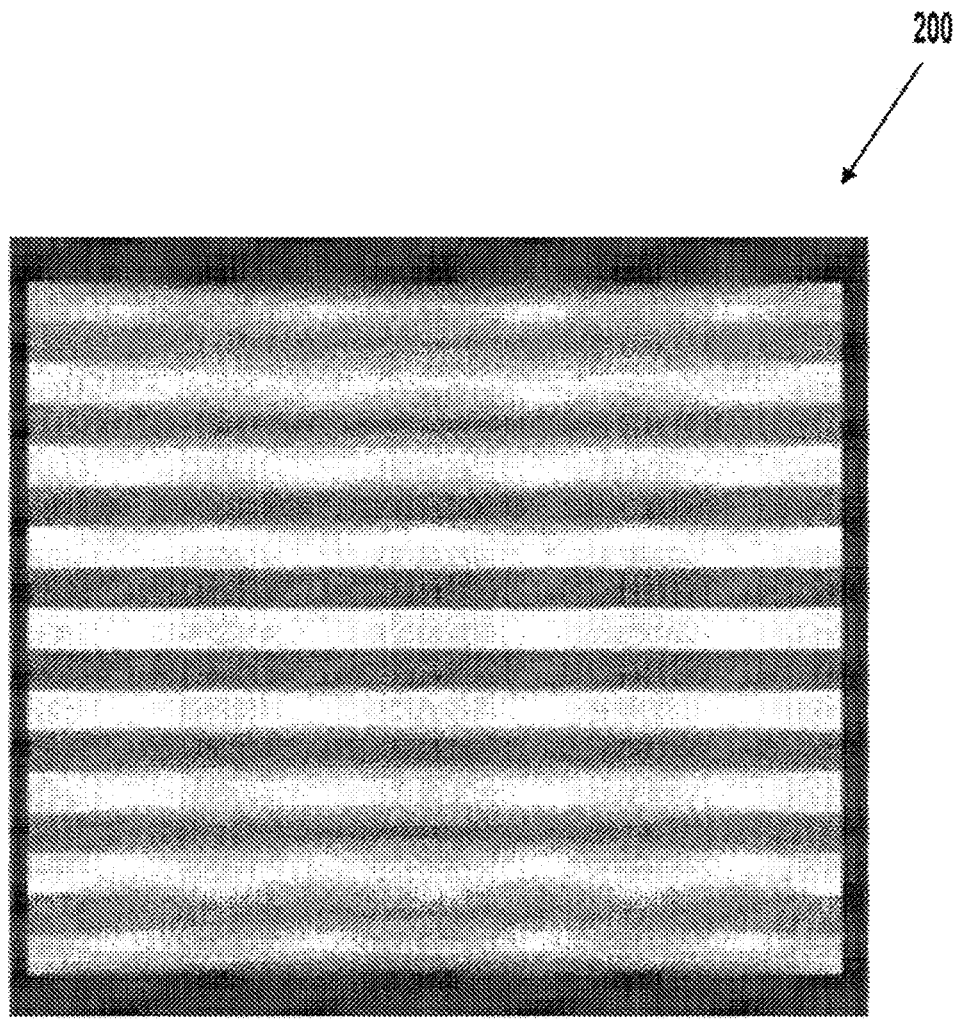
FIG. 2 depicts a cross-section of a cone beam 3D image of a disk phantom.

Referring also to FIG. 2, depicted is a cross-section of a cone beam 3D image 200 of a disk phantom, generated for example using a circular cone beam scan of FIGS. 1A-1C. As illustrated, there is an obvious degradation of spatial resolution in the vertical direction. The existence of the area 114 illustrated in FIG. 1C and the cone beam 3D image 200 of FIG. 2 illustrates the need to compensate for this area 114 using a suitable scanning technique or reconstruction approach or both to address this area 114.

One such approach, known as the Felkamp approach, uses approximation. Other approaches include compensating for the effect of the area 114 by additional motion of the X-ray emitter 102 and detector 104 along a different trajectory. However, no system is ideal. While making the circular motion described above with respect to FIGS. 1B and 1C, the motion of either the X-ray emitter 102 or the X-ray detector 104 can be corrupted by vibration or sag, for example due to wear of components. Further, if the object moves during a scan the resulted 3D image 200 can become corrupted.

Cone beam X-ray devices are popular and have commercial applications in numerous industries including but not limited to healthcare, the pharmaceutical industry, non-destructive quality control and quality analysis (QA), forensics, and so forth. There are multiple methods for system geometry registration when scanning one type of a phantom or another. Each method includes one or both of the following assumptions or restrictions: (a) the phantom is pre-defined and the design, geometry, and configuration are known a priori with a high level of mechanical precision, and/or (b) the system motion is nearly perfectly circular and only a few parameters describing or defining imperfections have to be calculated.

Additionally, there are numerous methods of object motion registration for further compensation, which can be separated into the general categories: (a) motion registration using techniques and equipment based on non-X-ray equipment, (b) motion registration using special markers (typically high-density markers) which are visible on the X-ray projections, and (c) motional registration based on internal sample structure analysis (e.g., human anatomy). Some commercial motion registration systems generate magnetic fields and use special sensors. Many commercial motion registration systems include motion capture systems that are based on stereoscopic principles and which include multiple high resolution video cameras working in the infra-red spectrum. However, multimedia approaches can be complex and expensive. Multimedia approaches require two separate tasks to be performed: (a) first the scanning system must be measured to determine how the scanning system moves in real-world X, Y, and Z coordinates, and (b) second, during an active phase of the scan, movement of the scanned object is captured by the video cameras or motion capture system. After the scan, these two geometry datasets are superimposed to produce the cone beam 3D image.

The CT reconstruction process of the present disclosure performs a scan that compensates for the movement of the scanned object without requiring a separate motion capture system. Assuming that the scanned object is rigid, and using the <X,Y,Z> coordinate system, the coordinates for any particular point of the scanned object do not change relative to one another. The X-ray detector can be assumed to be flat with its own local coordinate system <U,V>. For a system at a particular time t, when an X-ray projection is captured, any point belonging to the scanned object with coordinates <X,Y,Z> will be associated with the corresponding "shadow" on the detector plane with coordinates <U,V> as calculated by the following formulas:

$$U = \frac{A_{00}*X + A_{01}*Y + A_{02}*Z + A_{03}*1.0}{A_{20}*X + A_{21}*Y + A_{22}*Z + A_{23}*1.0}$$

$$V = \frac{A_{10}*X + A_{11}*Y + A_{12}*Z + A_{13}*1.0}{A_{20}*X + A_{21}*Y + A_{22}*Z + A_{23}*1.0}$$

where $A_{00} \ldots A_{23}$ are constants for this particular system position, and $A_{00} \ldots A_{23}$ can be defined as projection transformation matrix A. Thus for making a CT reconstruction when a scanning system and a scanned object make a motion of any type of complexity, it is sufficient to obtain X-ray 2-dimensional set of views plus projection transformation matrices A, with one matrix for every system position (every input 2-dimensional view.) Therefore collecting data about system motion and object motion can be performed using a single process, instead of two different processes that require applying two different techniques as described for the multimedia approaches.

Figure 3:
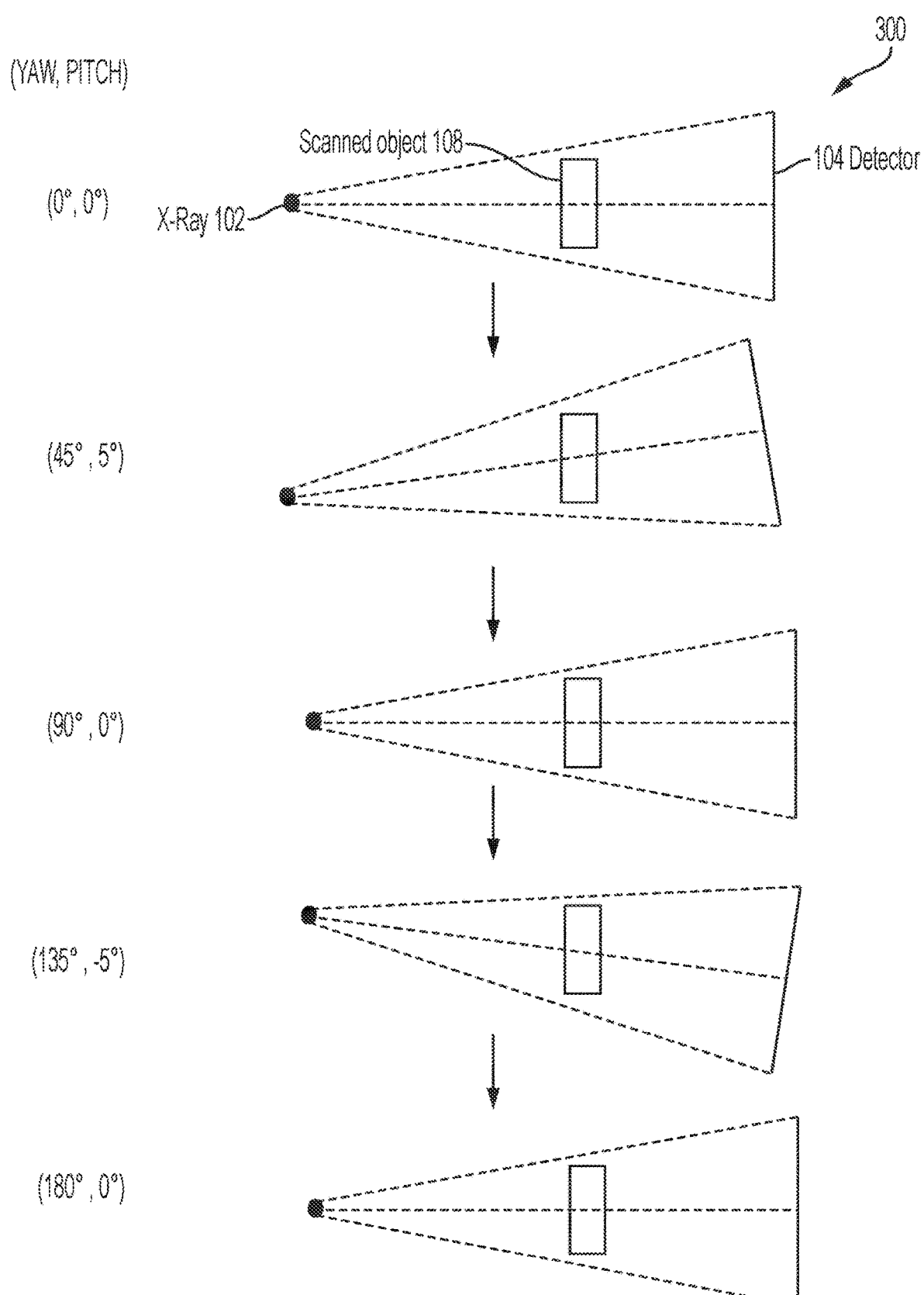
FIG. 3 depicts an embodiment of a complex scanning motion of the present disclosure.

Referring now to FIG. 3, an embodiment of a complex scanning motion 300 is presented. The complex scanning motion 300 can be most easily described using aviation terminology to describe the movement of the X-ray emitter 102 and X-ray detector 104. Assume that the X-ray emitter 102 represents an aircraft cockpit while the X-ray detector 104 represents the aircraft tail. The X-ray emitter 102 and X-ray detector 104 are fixed relative to one another and move in tandem. While the X-ray emitter 102 and X-ray detector 104 rotate about 180 degrees or more of "yaw", the X-ray emitter 102 and X-ray detector 104 also make a smooth sinusoidal "pitch" wobbling within a few degrees, for example 5-10 degrees. As illustrated in FIG. 3, the scanned object 302 is viewed from the side as the X-ray emitter 102 and X-ray detector 104 move through 180 degrees of yaw, and the X-ray emitter 102 and X-ray detector 104 wobble in a sinusoidal motion from a maximum of about 5 degrees when yaw is at 45 degrees to a minimum of −5 degrees when yaw is at 135 degrees, and passing through 0 degrees when the yaw is at 0 degrees, 90 degrees, and 180 degrees. The yaw and pitch angles presented above are intended only to illustrate the motion of the X-ray emitter 102 and X-ray detector 104, and are not intended to limit the disclosure to any specific angular motions.

Figure 4:
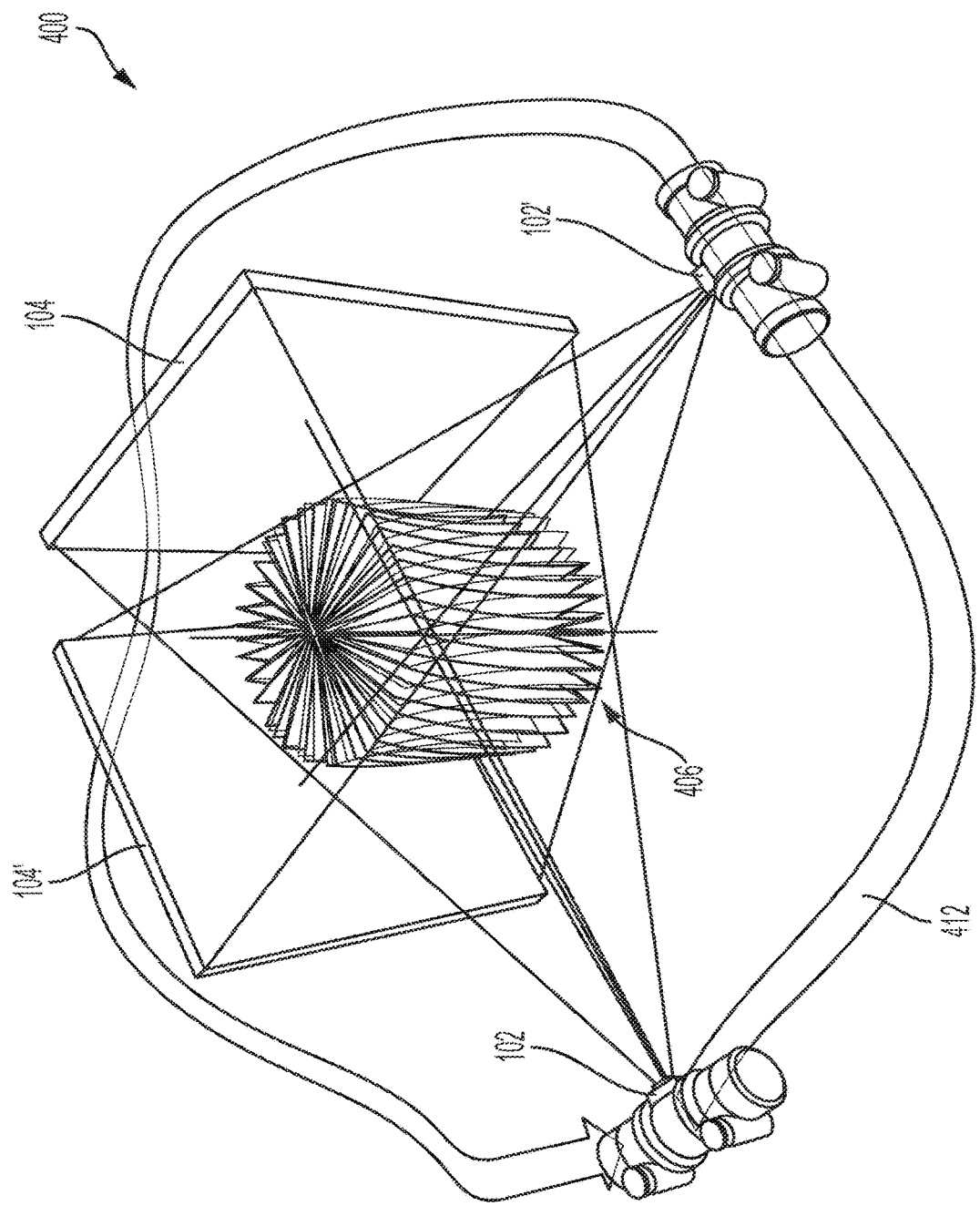
FIG. 4 illustrates an embodiment of a complex curvilinear path of an X-ray emitter and X-ray detector.

Referring now also to FIG. 4, the complex curvilinear path 412 of an X-ray emitter 102 and X-ray detector 104 following the complex scanning motion of FIG. 3 is presented. Advantageously, after all of the projections 406 have contributed to the Fourier spectrum, there is no area of the spectrum which is not defined. The complex scanning motion therefore advantageously improves the spatial resolution of the resulting cone beam 3D image.

Figure 5A:
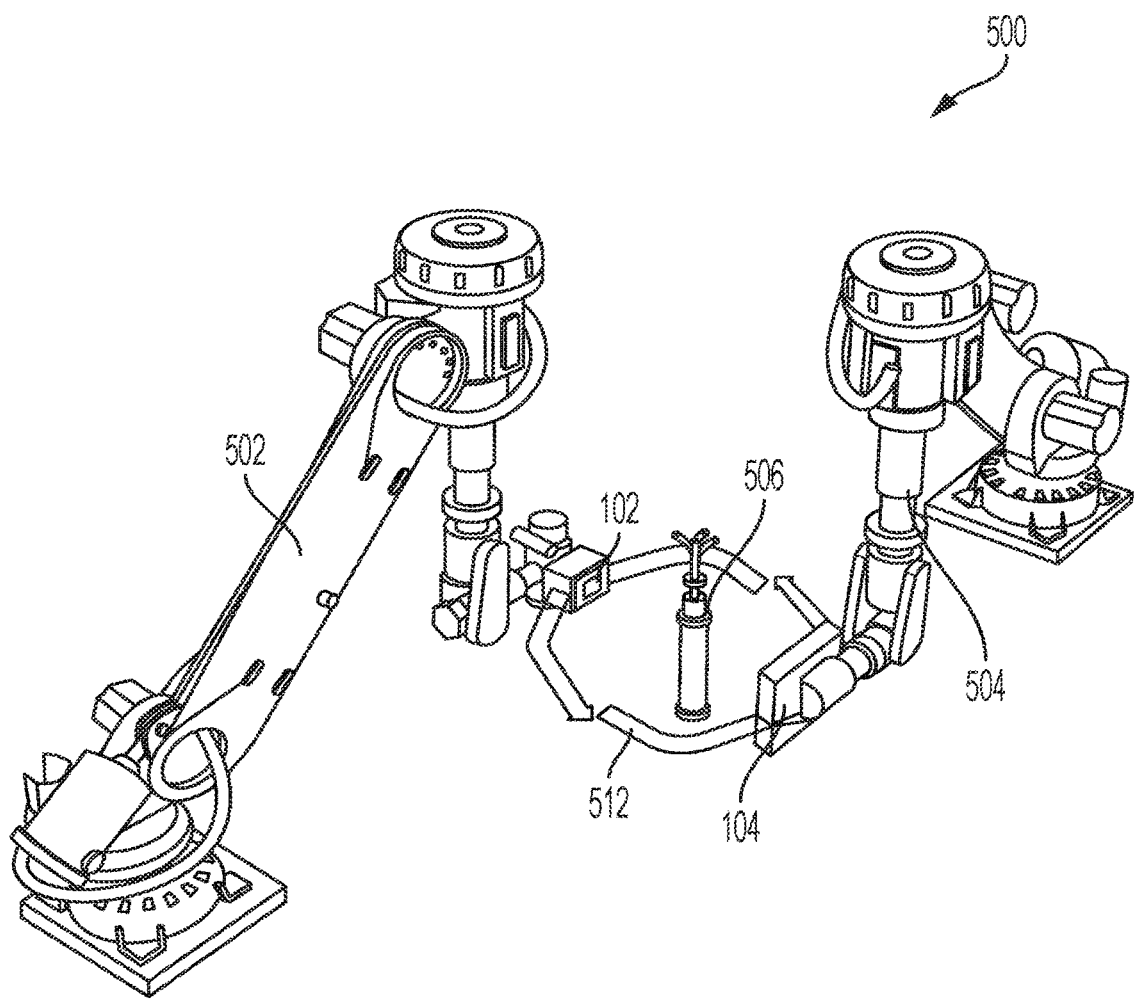
FIG. 5A depicts an embodiment of a two-arm robotic scanning system.
Figure 5B:
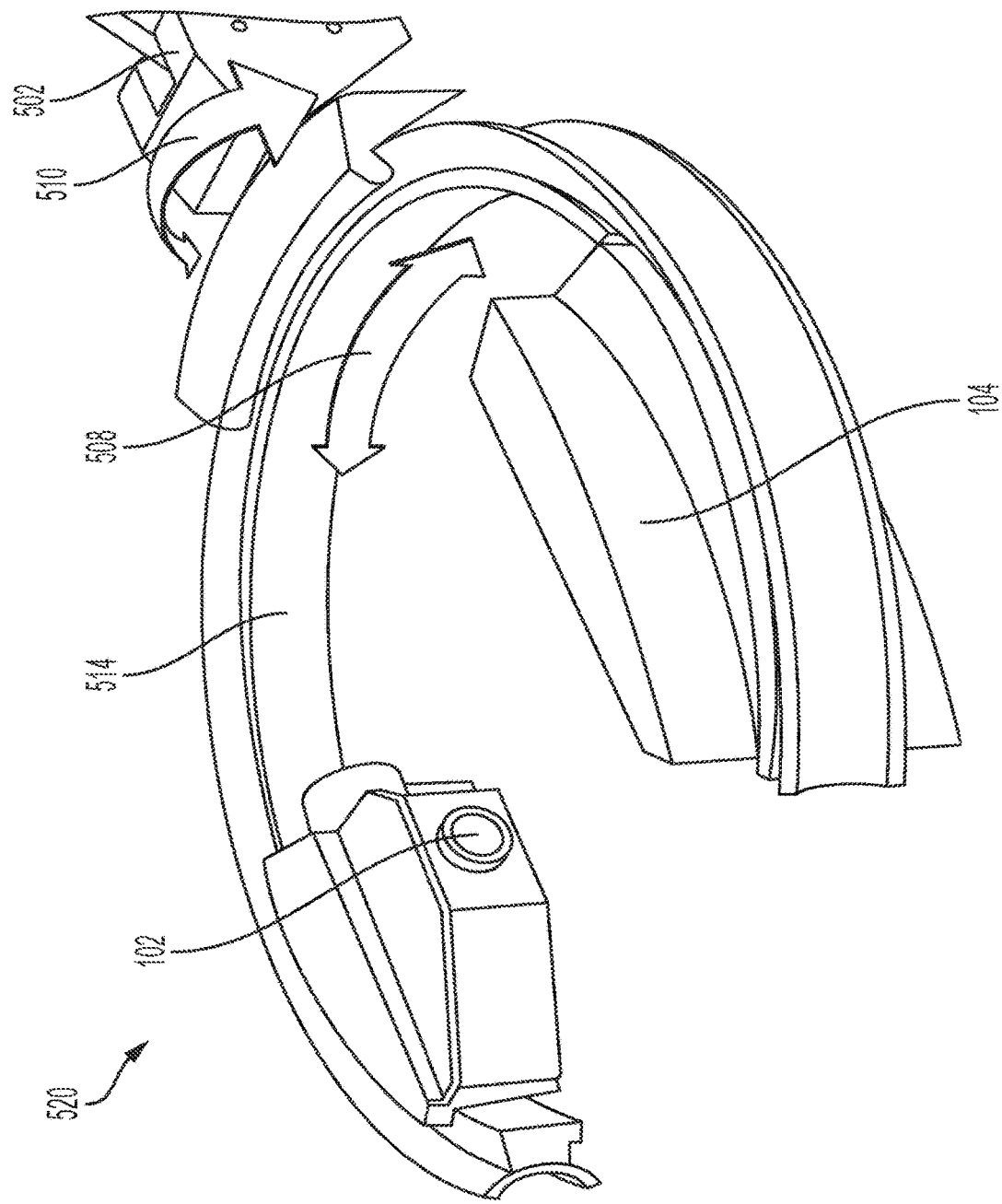
FIG. 5B depicts an embodiment of a single-arm robotic scanning system.

FIGS. 5A and 5B depict example embodiments of robotic scanning systems 500, 520 that can be configured to perform the complex scanning motion described above with regard to FIGS. 3 and 4. FIG. 5A illustrates a two-arm robotic scanning system 500 whereby a first robotic arm 502 controls the movement of the X-ray emitter 102 and a second robotic arm 504 controls the movement of the X-ray detector 104. The first robotic arm 502 and the second robotic arm 504 coordinate the movements of the X-ray emitter 102 and the X-ray detector 104 to follow the complex curvilinear path 512 when scanning an object 506.

FIG. 5B illustrates a single-arm robotic scanning system 520. A robotic arm 502 articulates and moves a C-Arm 514 capable of rotating in a first angular direction 508 and a second angular direction 510. The robotic arm 502 and rotatable C-Arm 514 permit the single-arm robotic scanning system 520 to track a desired curvilinear path through a full 360-degree arc about the object and correctly position the X-ray emitter 102 and the X-ray detector 104 relative to the object to be scanned.

In a first embodiment, the motion of the robotic scanning systems 500, 520 can be captured, for example using suitable motion tracking systems, and converted into projective transformation matrices described above for performing the CT reconstruction.

In a second embodiment, markers (e.g., fiducials or high-density beads) associated with an object to be scanned can be used to determine the motion of the robotic scanning systems 500, 520. Motion of the object being scanned can also be determined. Marker coordinates $<U,V>$ within the X-ray detector 504 plane can be algorithmically detected. The detected $<U,V>$ coordinates can then be used to calculate the projective transformation matrices.

Figure 6:
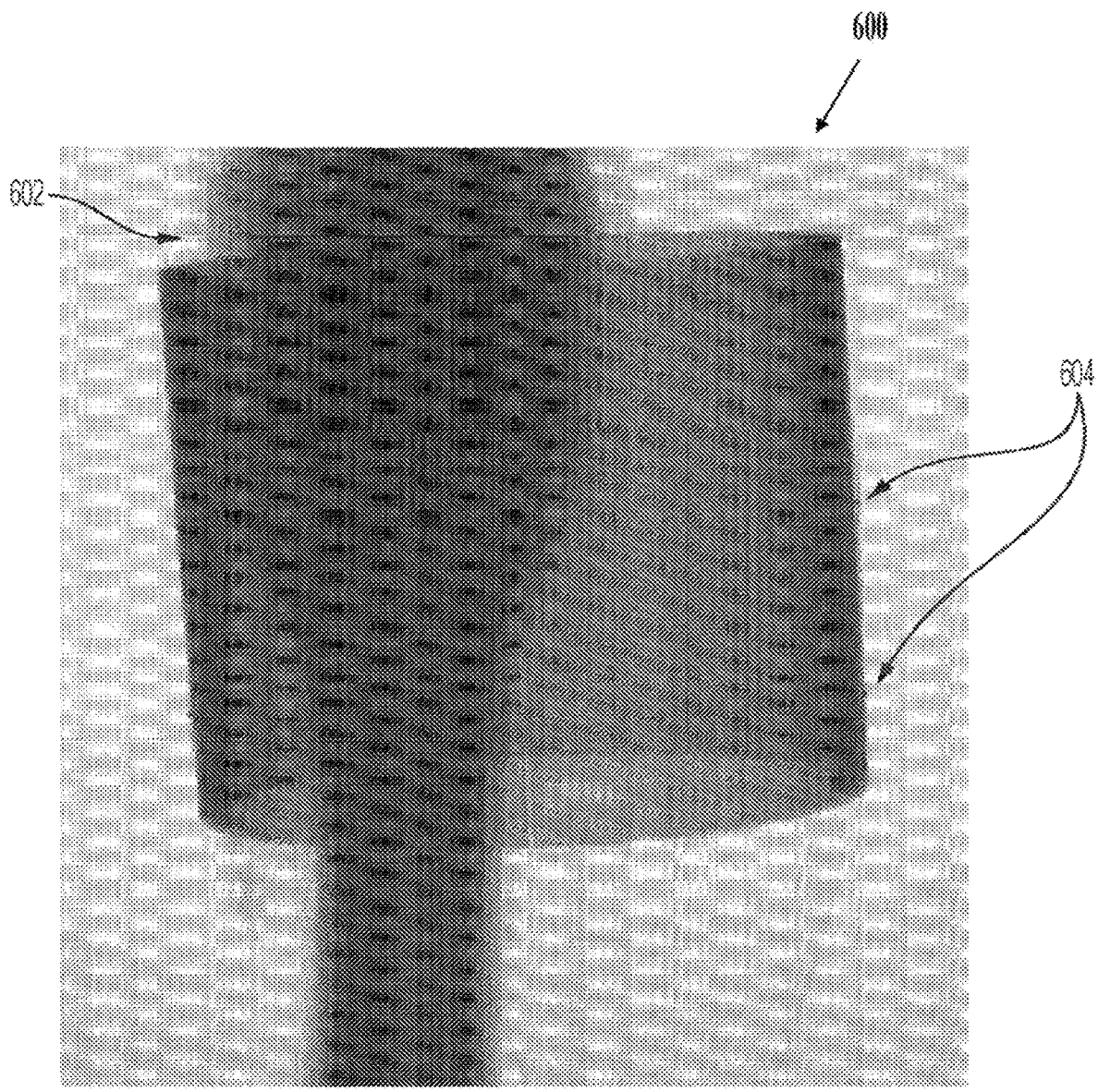
FIG. 6 depicts an X-ray intensity image of an object and fiducials.
Figure 7:
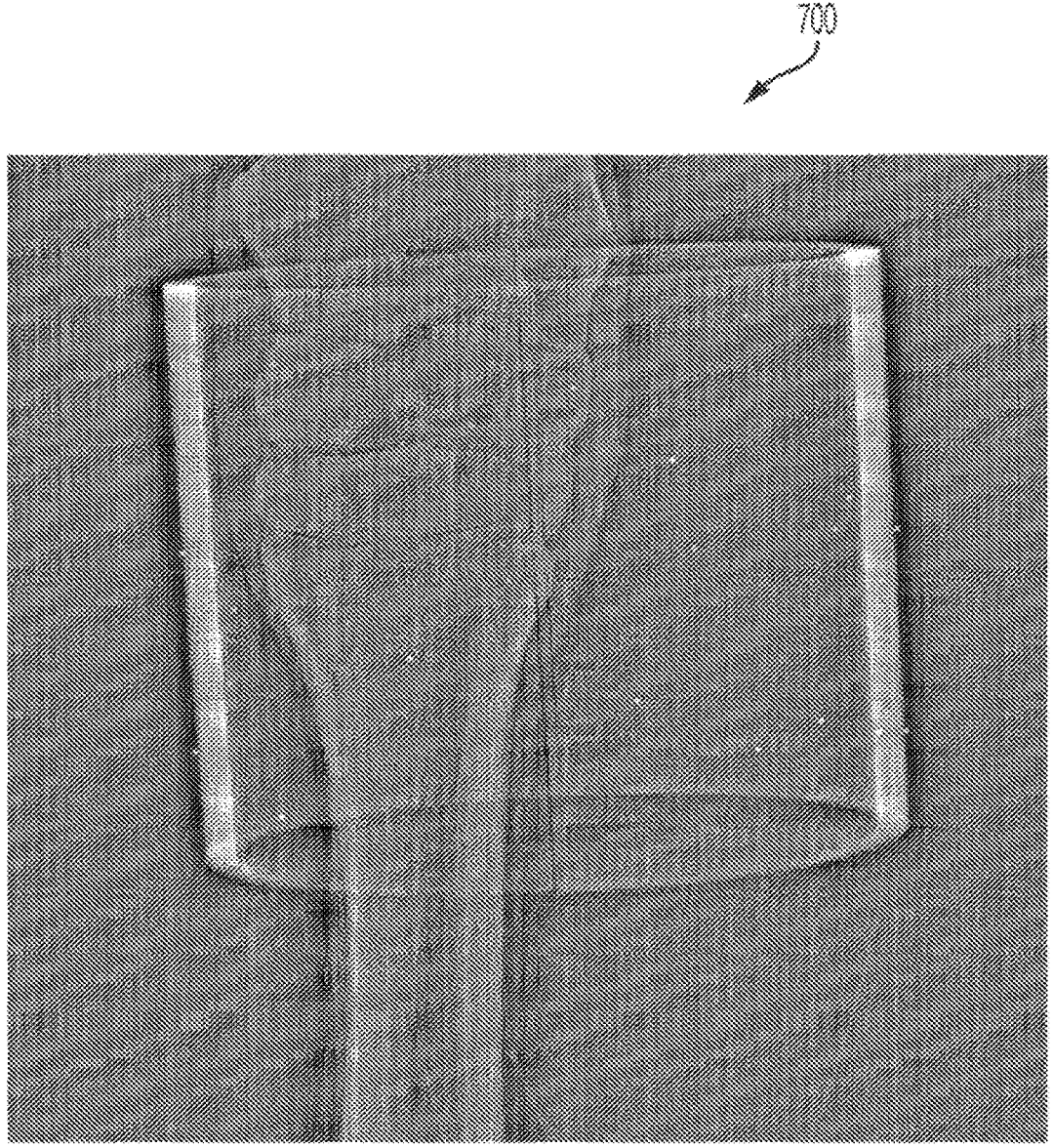
FIG. 7 depicts a processed X-ray view of the object and fiducials of FIG. 6.

The robotic scanning system 500, 520 first scans an object to produce an X-ray intensity image 600 of the object being scanned 602 and the markers 604 as illustrated in FIG. 6. The X-ray intensity image 600 of FIG. 6 is converted into a logged attenuation representation 700 as illustrated in FIG. 7. A non-linear two-dimensional high-pass filter enhances the markers 800 that permits software to determine the positions of the markers to calculate the projective transformation matrices.

An embodiment of a non-linear two-dimensional high-pass filter can be defined as follows. A circle with radius R around a point $<U_0,V_0>$ within the X-ray detector plane defines a set of pixels, $\Omega$, on the X-ray detector plane. The set $\Omega$ consists of the points located at distance R from pixel $<U_0,V_0>$ as defined by the equation:

$$<U,V> \in \Omega | \sqrt{(U_0-U)^2+(V_0-V)^2}-R<1$$

The points $\Omega$ can be represented as the list with elements $<U,V,S>$ where S is the value of the image at point $<U,V>$. The median signal $S_M$ can be defined as:

$$S_M = S_{UV}\left|\sum_{i|S_{UV}<S_M} 1 - \sum_{i|S_{UV}\geq S_M} 1\right| \leq 1$$

Figure 8:
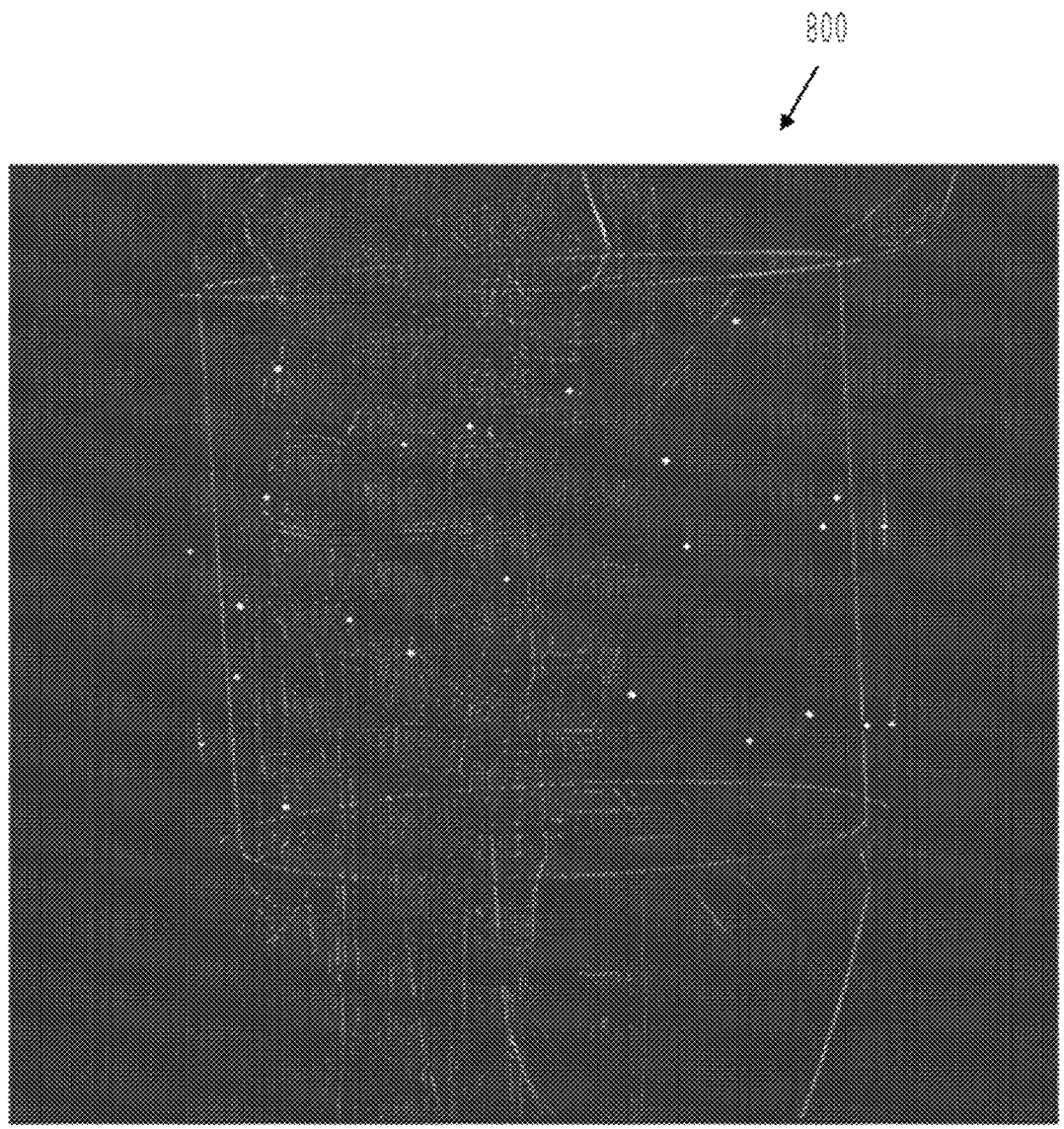
FIG. 8 depicts a filtered X-ray for enhancing the fiducials of FIGS. 6 and 7.

Assuming $S_{(M,U0,V0,R0)}$ is a median signal corresponding to the point $<U_0,V_0>$ and radius $R_0$, and assuming that $S_{M,U0,V0,R1}$ is a median signal corresponding to the point $<U_0,V_0>$ and radius $R_1$. Then the response of the nonlinear filter at the point $<U,V>$ is:

$$R_{UV} = \max_{R_0<A, R_1<A} |S_{(M,U,V,R0)} - S_{(M,U,V,R1)}|$$

where A is the filter aperture. By setting appropriate thresholds, a set of marker coordinates can be obtained algorithmically from the filtered image, for example as depicted in FIG. 8.

An embodiment of an algorithm for calculating projection transformation matrices from a set of projected marker coordinates is presented below. Applying the non-linear two-dimensional high-pass filter above produces a set of marker shadows $<U^n_i, V^n_i>$, where index n corresponds to a frame number and index i corresponds to a marker number within a frame. Assuming that the system motion is "smooth", for example the X-ray source and X-ray detector follow a curvilinear path during the scan, and neither the object nor the X-ray source and detector make "sharp" (highly accelerated/decelerated) moves, then any element $A^n_{ij}$ of projection transformation matrix at the system angular position n (=frame number) can be represented as:

$$A_{ij}^n = S_{ij}^T(n)$$

Where $S_{ij}^T$ is a spline interpolation of matrix element $A_{ij}$. T as a superscript indicates that a spline has T knots. This equation can be rewritten as:

$$S_{ij}^T = S(K_{ij}^0, K_{ij}^1, \ldots, K_{ij}^T)$$

Every marker has coordinates in the object space $<X_m, X_m, Z_m>$ where m=0, ... M−1. This provides a highly redundant system of nonlinear equations:

$$U_m*(A_{20}*X_m A_{21}*Y_m+A_{22}*Z_m+A_{23})-A_{00}*X_m+A_{01}*Y_m+A_{02}*Z_m+A_{03}=0$$

$$V_m*(A_{20}*X_m A_{21}*Y_m+A_{22}*Z_m+A_{23})-A_{10}*X_m+A_{11}*Y_m+A_{12}*Z_m+A_{13}=0$$

where $U_m$, $V_m$ are known and $X_m$, $X_m$, $Z_m$, $A_{ij}$ are unknown.

Thus, a full system (source, detector, object) motion can be defined and described by a relatively small number of factors: 11 matrix coefficients based on (containing) T knots. In an example system, if there are 500 projections, 20 markers, and 12 knots as spline complexity factors, then the system will contain [2*20*500=20000] equations with [2*20*500=20000] known values and [11*20+20*3=280] unknown values. The high redundancy of the system allows the system designer to employ known algorithms and methods to resolve these equations with high level of accuracy and robustness even if the known data $U_m$, $V_m$ contain a substantial portion of corrupted measurements.

Figure 9A:
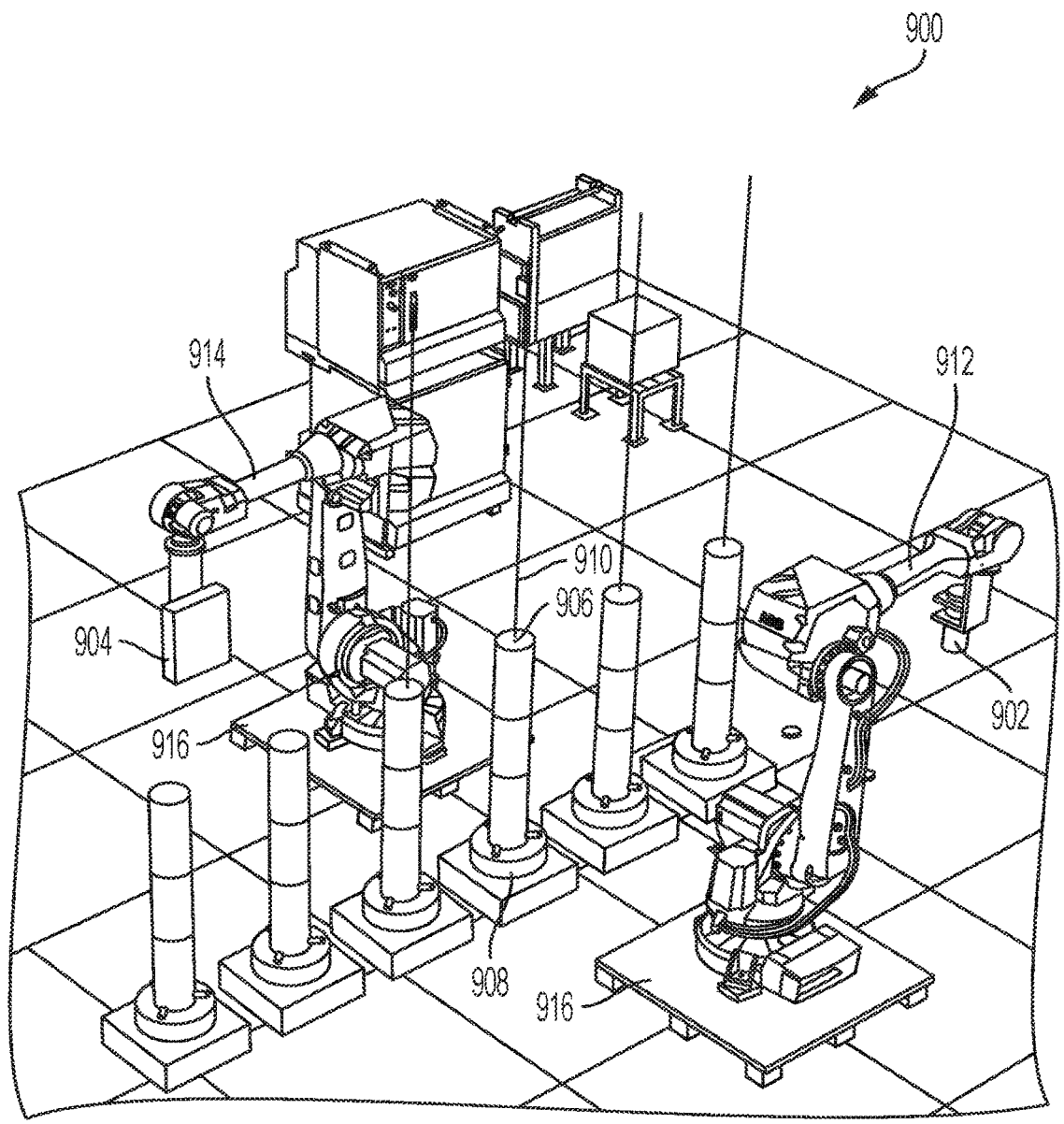
FIG. 9A depicts an embodiment of a two-arm CT core sample scanning system for a plurality of core samples.

Referring now to FIG. 9A, a two-arm CT core sample scanning system 900 is presented. The system 900 includes an X-ray emitter 902 coupled to a first robotic arm 912, and an X-ray detector 904 coupled to a second robotic arm 914. Each of the robotic arms 912, 914 can articulate and rotate with six degrees of freedom, allowing movement of the X-ray emitter 902 and X-ray detector 904 in the x, y, and z directions as well as rotation about three perpendicular axes that is commonly referred to as pitch, yaw, and roll. The robotic arms 912, 914 can be configured in a master-slave mode as would be understood in the art. In this configuration, one of the robotic arms 912, 914 is the master robotic arm and synchronizes movements of both the master and slave robotic arms. Communications between the robotic arms 912, 914 can include serial communications or Ethernet based communications among other suitable communication protocols.

Figure 9B:
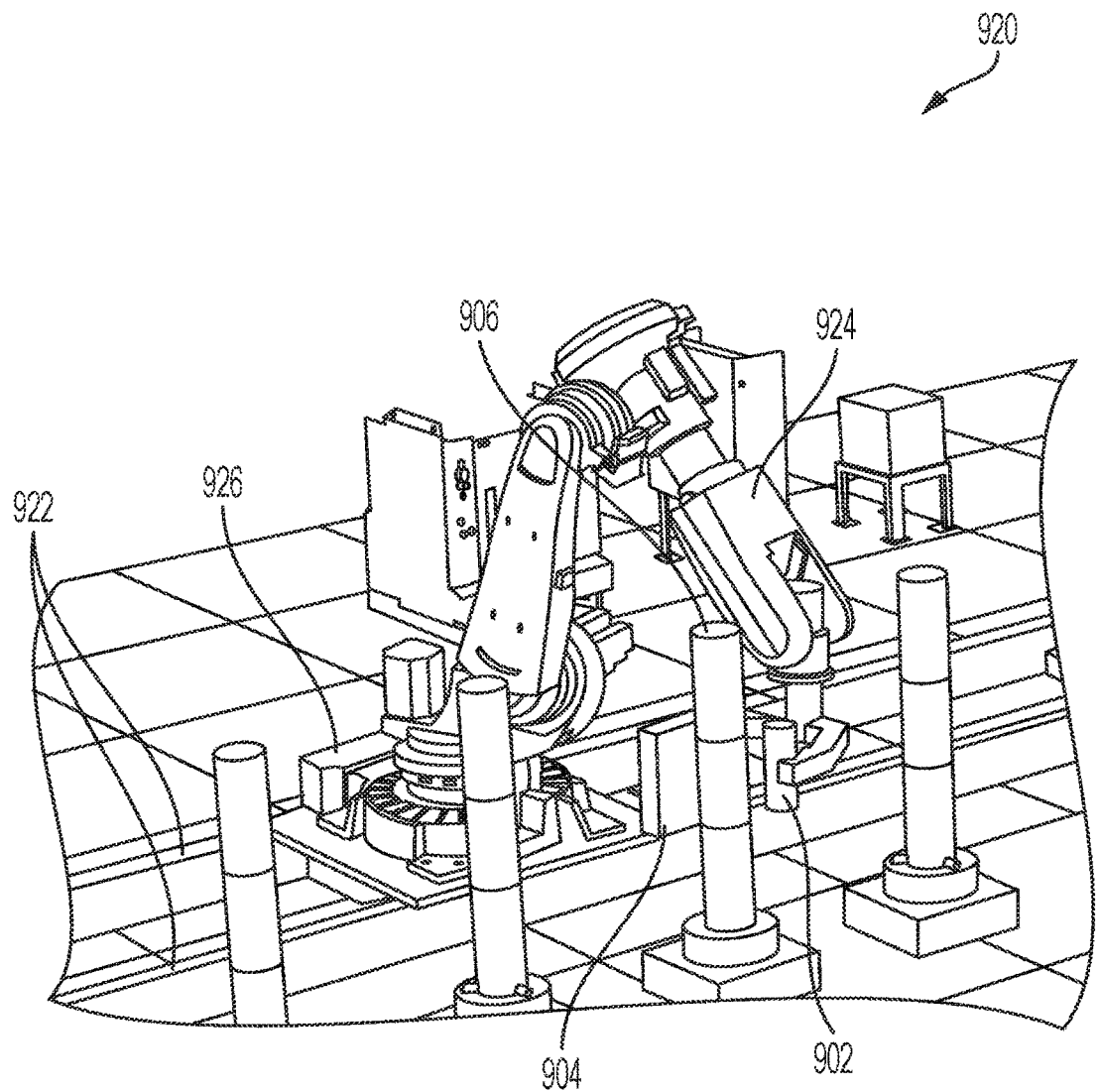
FIG. 9B depicts an embodiment of a movable single-arm CT core sample scanning system for a plurality of core samples.

In the embodiment illustrated in FIG. 9A, the first robotic arm 912 and the second robotic arm 914 are each secured to a respective fixed base 916. In alternative embodiments, tracks or other means for moving the robotic arms 912, 914 can be substituted for the fixed bases 916 to facilitate movement between core samples 906 and permit the system 900 to monitor larger numbers of core samples 906. For example, as illustrated in FIG. 9B, a single-arm CT core sample scanning system 920 has a single robotic arm 924 that is configured with a C-arm 928 having both an X-ray emitter 902 and an X-ray detector 904. A movable base 926 is positioned on a rail system or track 922 that, using suitable controllers, allows the single robotic arm 924 to be repositioned along the track 922 in proximity to a core sample 906 to be scanned.

Example robotic arms 912, 914 include the 4600 series from ABB which allow repeatable repositioning to within approximately 5 microns, allowing images in subsequent scans to be within about 20 microns of previous scans. The 4600 series robotic arms 912, 914 allow for precision scanning of 1.5 to 6 inch cores using X-ray emitters 902 capable of several hundred watts of continuous power. The type of robotic arms 912, 914 that can be used depends on the required positioning resolution of the robotic arms 912, 914, the size and weight of the X-ray emitter 902 and X-ray detector 904, and the size of the core sample 906 to be scanned. For example, for inch or half-inch cores, micro-CT scanners having low power CT tubes can be used which allow for smaller robotic arms. Micro CT scanners can often achieve 12-micron resolutions or better. Future robotic arms 912, 914 may be able to provide repeatable positioning and image down to 1-2 microns or better. In still other embodiments, the robotic arms 912, 914 can be repositioned with a precision of approximately 1/10 mm, permitting images in subsequent scans to be within approximately 1/4 mm.

A plurality of core samples 906 can be monitored by the system 900 and are positioned between the robotic arms 912, 914. The core samples are spaced apart from one another to allow the robotic arms 912, 914 to move between and scan each of the core samples 906. Each of the core samples 906 is secured inside a metal sleeve and secured to a base 908. High temperature, high pressure lines 910 can be attached to the top (shown) and bottom (not shown) of the core samples 906 to assist in determining the properties of material in the core samples 906 for example capillary pressure, density, and immiscibility, as previously described. Soaps, alcohols, or liquid $CO_2$ can be introduced through the lines 910 to assist in determining how best to extract substances from the ground associated with the core samples 906. During experiments, which can be run over a period of days or weeks, the core samples 906 can be periodically scanned by the system 900 as describe in greater detail below with regard to FIGS. 10-13. Advantageously, CT scanning of the core samples 906 allows for repeated, non-invasive and non-destructive analysis of each of the core samples 906.

Figure 10:
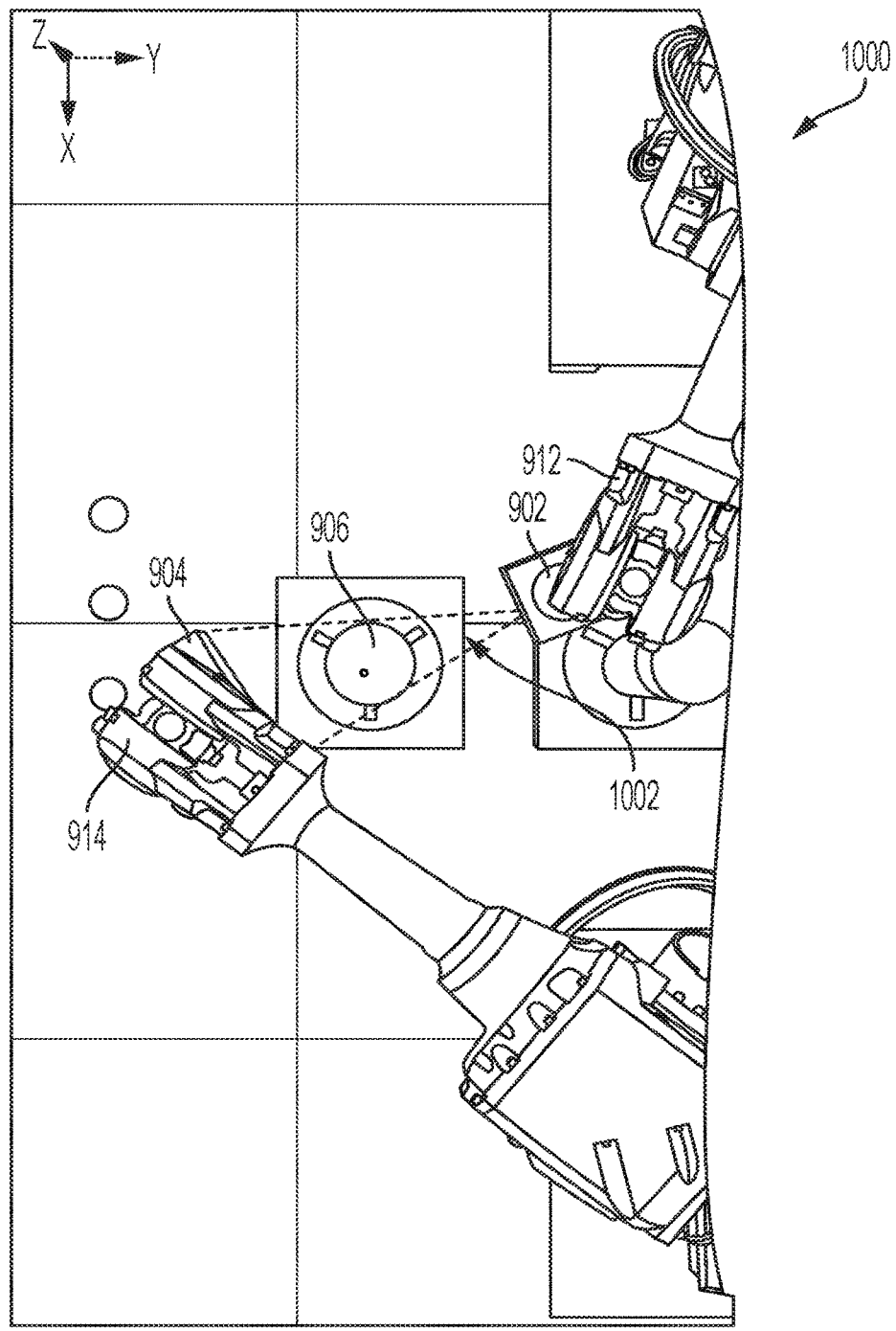
FIG. 10 depicts example robotic arm positions during a scan of a sample core by a two-arm CT core sample scanning system.

Referring now also to FIG. 10, illustrate are example robotic arm positions during a scan 1000 of a core sample 906 for a two-arm CT core sample scanning system. To begin scanning the selected core sample 906, the first robotic arm 912 positions the X-ray emitter 902 on one side of the core sample 906 and the second robotic arm 914 positions the X-ray detector 904 on the other side of the core sample 906. The X-ray emitter 902 is turned on to emit a cone beam 1002 and the X-ray detector 904 detects X-ray emissions through the core sample 906. The relative positions of the X-ray emitter 902 and X-ray detector 904 are described in addition detail with regard to FIG. 12 below.

Figure 11:
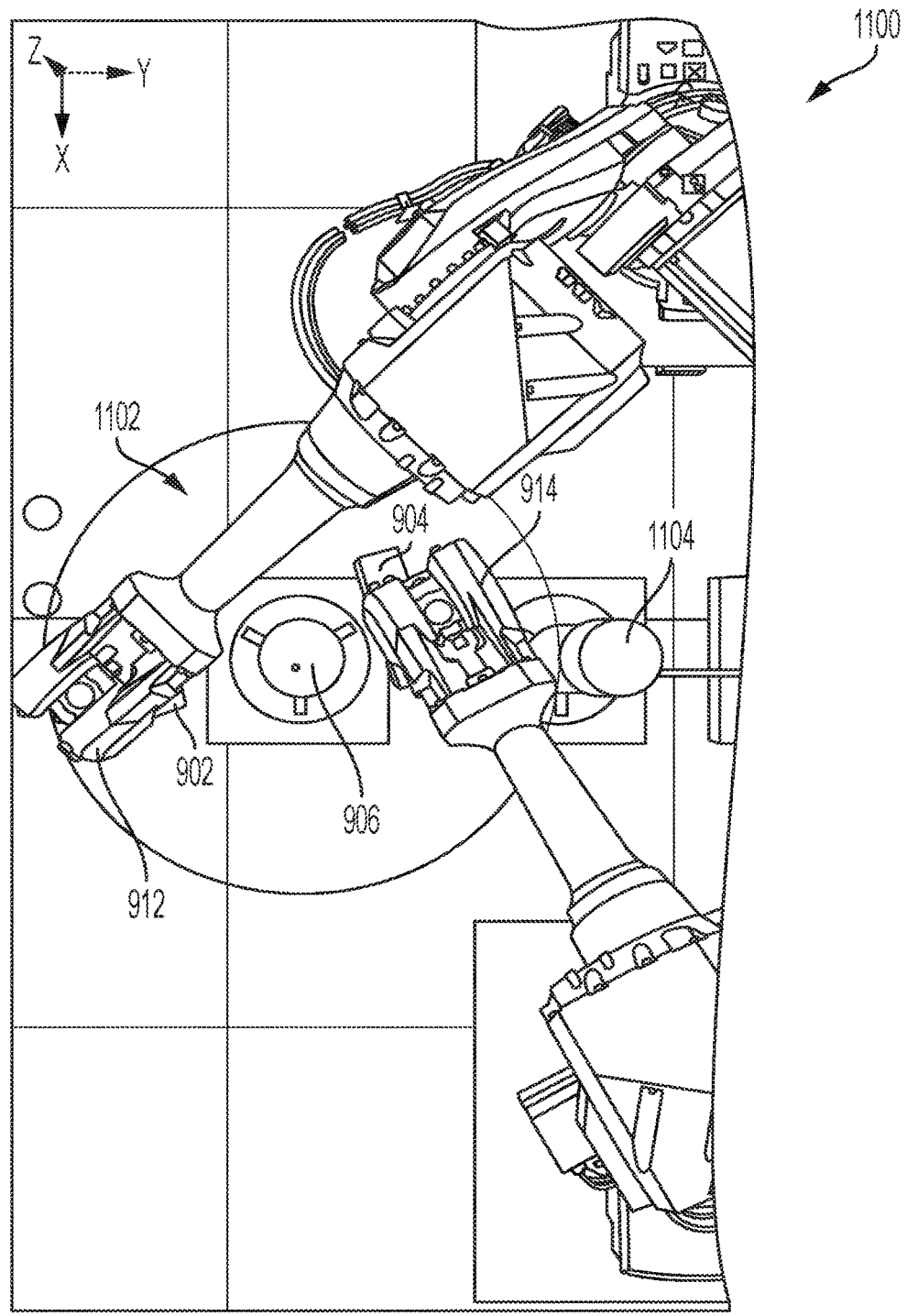
FIG. 11 depicts the range of robotic arm positions around a sample core during a scan by a two-arm CT core sample scanning system.

Referring also to FIG. 11, the robotic arms 912, 914 move the X-ray emitter 902 and the X-ray detector 904 in complementary orbits around the core sample 906 during a scan 1100 to generate additional surfaces or 2-dimensional views used in image reconstruction. The orbital paths move the X-ray emitter 902 and X-ray detector 904 through arcs of approximately 220 degrees or more, allowing the core sample 906 to be imaged sufficiently for CT reconstruction. The complementary orbits are described in additional detail with regard to FIG. 12 below. The combined arm range 1102 of the robotic arms 912, 914 approximates a cylinder around the core sample 906. Adjacent core samples 1104 are positioned such that the robotic arms 912 will not hit the adjacent core samples 1104 during scanning of the core sample.

Figure 12:
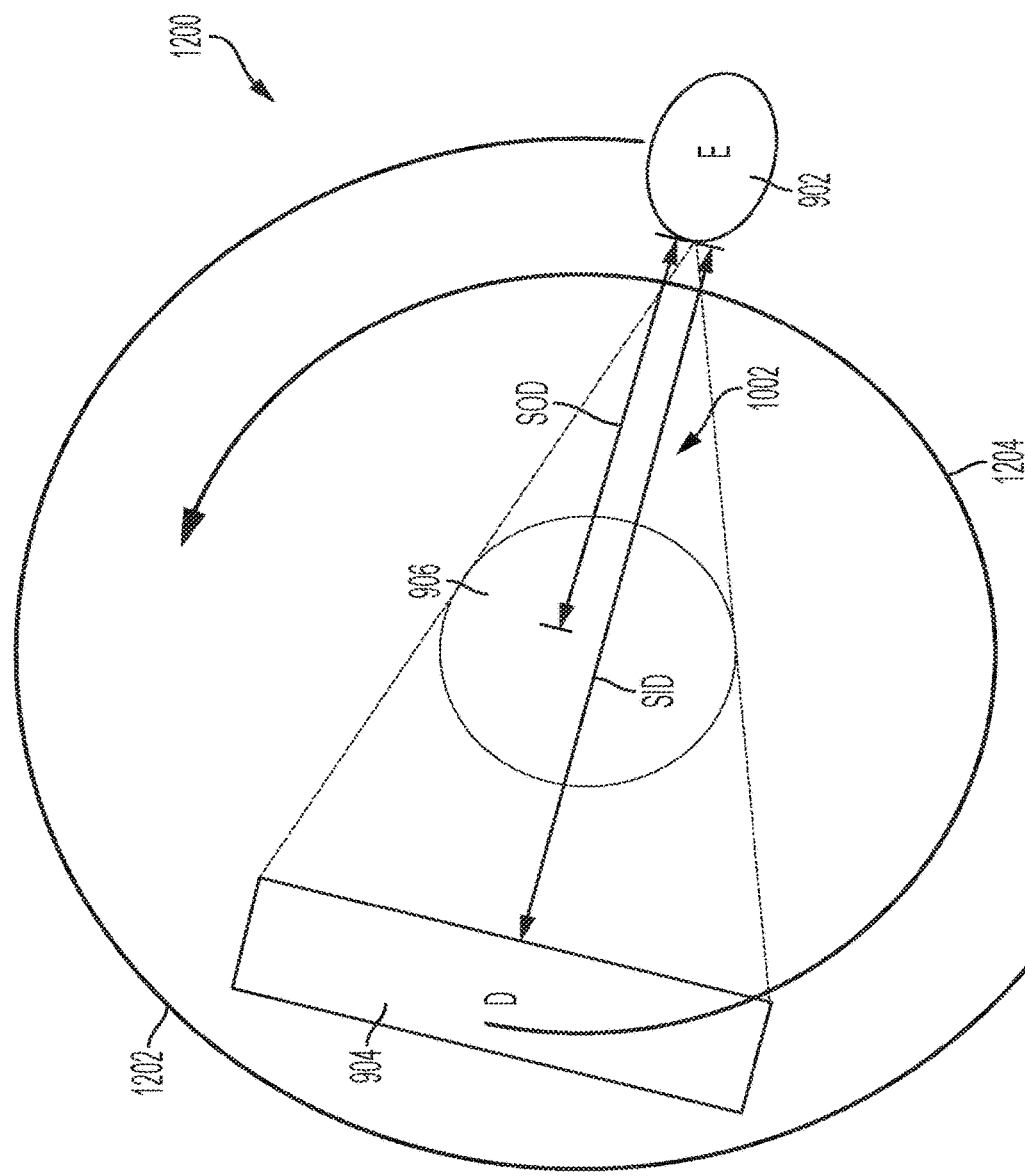
FIG. 12 depicts the relative positions and orbital paths of the robotic arms around a sample core during a scan by a two arm CT core sample scanning system.

FIG. 12 illustrates the relative positions and orbital paths of the X-ray emitter 902 and X-ray detector 904 during a scan 1200 of the core sample 906. To maximize resolution of the CT reconstruction, the X-ray emitter 902 and X-ray detector 904 are positioned such that the CT scan cone 1002 causes all or most of the X-ray detector 904 to be used. This is the magnification level which is defined as SID/SOD, which is the source image distance (SID) between the X-ray emitter 902 and the X-ray detector 904 divided by the source object distance (SOD) between the X-ray emitter 902 and the object as illustrated in FIG. 12. Depending on the magnification, the distance from the X-ray detector 904 to the core sample 906, may be different than the distance from the X-ray detector 904 to the core sample 906. Therefore, the emitter orbital path 1202 can be different from the detector orbital path 1204 as illustrated, however the emitter orbital path 1202 and detector orbital path 1204 will be complementary to one another. Generally, the magnification level is kept constant during scans, however the use of separate robotic arms 912, 914 permits variable magnification or dynamic magnification. In an embodiment, a single robotic arm configured with an adjustable C-arm can similarly be used for CT scans and also achieve variable magnification.

Accommodating core samples in traditional CT scanning apparatuses presents logistical challenges. Core samples are generally very heavy, making it difficult to move core samples into position for scanning by a traditional CT scanner. Further complicating movement of the core samples is accommodating the high temperature, high pressure lines that are typically present during testing. Moreover, cores are typically mounted inside of a metal sleeve, often with a rubber liner which can allow the cores to move when repositioned. Advantageously, by moving the robotic arms 912, 914 instead of the core samples 906, the material in the core samples 906 is less likely to move, allowing subsequent scans of the core samples 906 to align with previous scans, which facilitate analysis of changes in the core samples 906 as a result of experiments run on the core samples 906. However, it is possible for core samples 906 to shift over time, and to precisely align scans the robotic arms 912, 914 may need to take slightly different orbital paths in subsequent scans from the initial scan. While robotic arms are generally uniformly repositioned, there still may be some variation in relative positions between a core and scanning apparatus for a stationery core. Software correction is suitably implemented to compensate for variations between a core and scanner. This is suitably accomplished by use of a known core sample feature of either the core itself or a feature or making on the core casing. Compensation may be in the form of modified scanning apparatus movement as noted above, or algorithmic compensation on captured imaging.

Figures 13A, 13B:
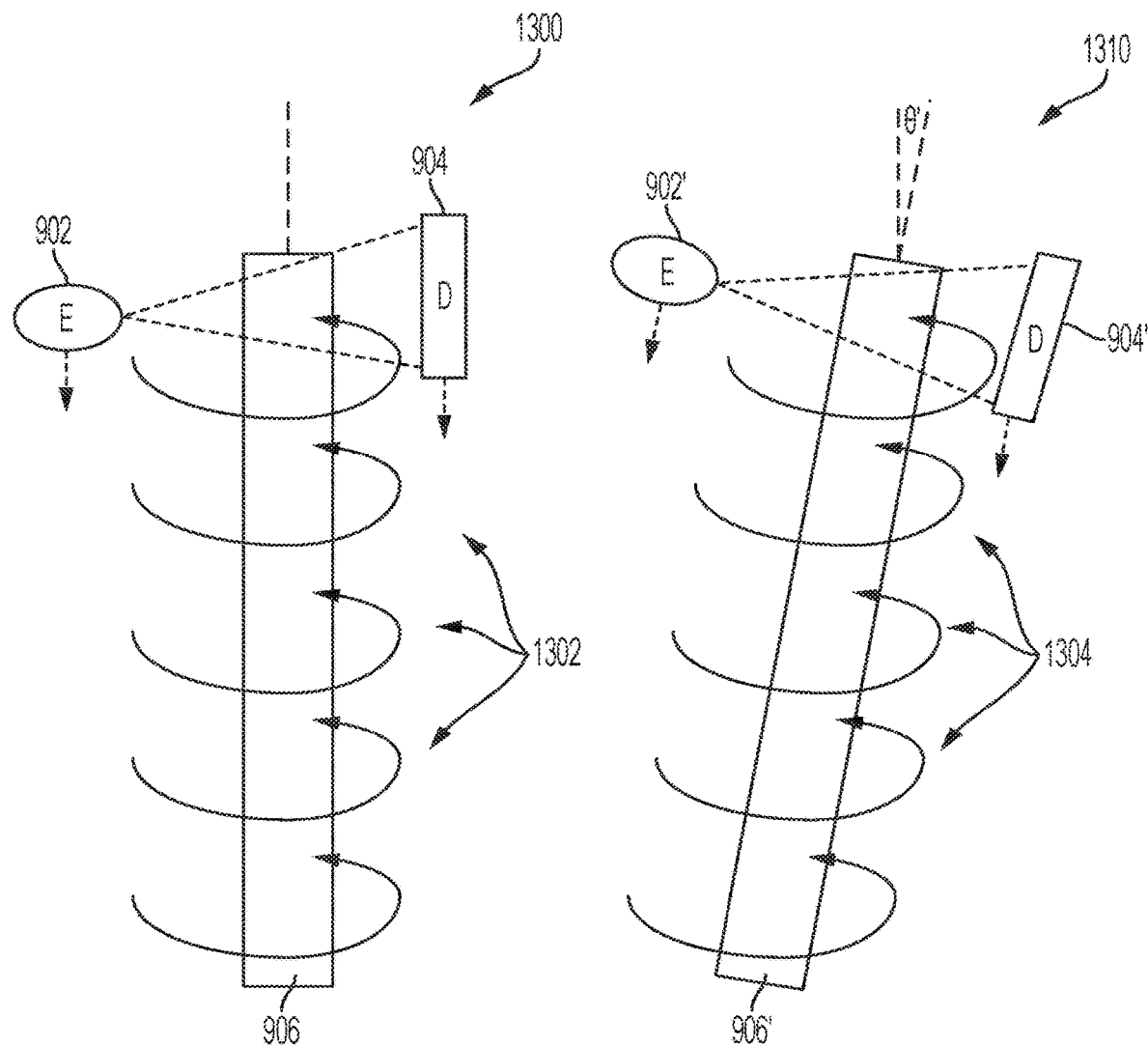
FIG. 13A depicts the position of a sample core during an initial scan by a CT core sample scanning system.
FIG. 13B depicts the position of the sample core during a subsequent scan by the CT core sample scanning system.

Referring now to FIGS. 13A and 13B, positions of the same core sample 906, 906' during an initial scan 1300 and a subsequent scan 1310 are illustrated. In the initial scan 1300 of FIG. 13A, the core sample 906 has a first alignment, illustrated here as vertical only for purposes of explaining a concept of the disclosure. During the initial scan 1300, the X-ray emitter 902 and X-ray detector 904 are moved in their respective orbital paths 1302 at a plurality of vertical heights over the length of the core sample 906. In a subsequent scan 1310 illustrated in FIG. 13B, the core sample 906' has changed position slightly, for example by tilting slightly at angle θ as illustrated. The controller (not shown) recalculates the orbital paths 1304 and pitch, yaw, and roll of the X-ray emitter 902 and X-ray detector 904 in order to maintain the same spatial positioning of the X-ray emitter 902 and X-ray detector 904 relative to the core sample 906' in the subsequent scan 1310 as in the initial scan 1300 of the core sample 906.

In order determine the position of the core sample 906, 906' for each of the scans 1300, 1310 the controller performs multiple scans one or more scout scans using a reduced number of projections followed by a full production scan. Whereas a production scan is a precise scan that may take 20 minutes or more to complete, each scout scan may take just a minute or more as the scout scans are used primarily to determine the position and alignment of the core sample 906, 906'. Once the scout scans are complete, the controller calculates the precise adjustments to the orbital paths 1302, 1304 necessary for the full production scan and the full production scan is executed by the controller.

In an embodiment, the sleeve of the core sample 906, 906' can include features that assist with the scout scans as would be understood in the art, such as marks, indentations, scoring, fiducials, high density beads, and so forth. For example, these features can provide marker coordinates within the X-ray detector plane that can be algorithmically detected. The detected coordinates can then be used to calculate the position and alignment of the core sample 906, 906'. The X-ray intensity image in the scout scan can be converted into a logged attenuation representation. A non-linear two-dimensional high-pass filter can enhance the features and permit the controller to determine the positions of the features to calculate the position and alignment of the core sample 906, 906'.

Figure 14:
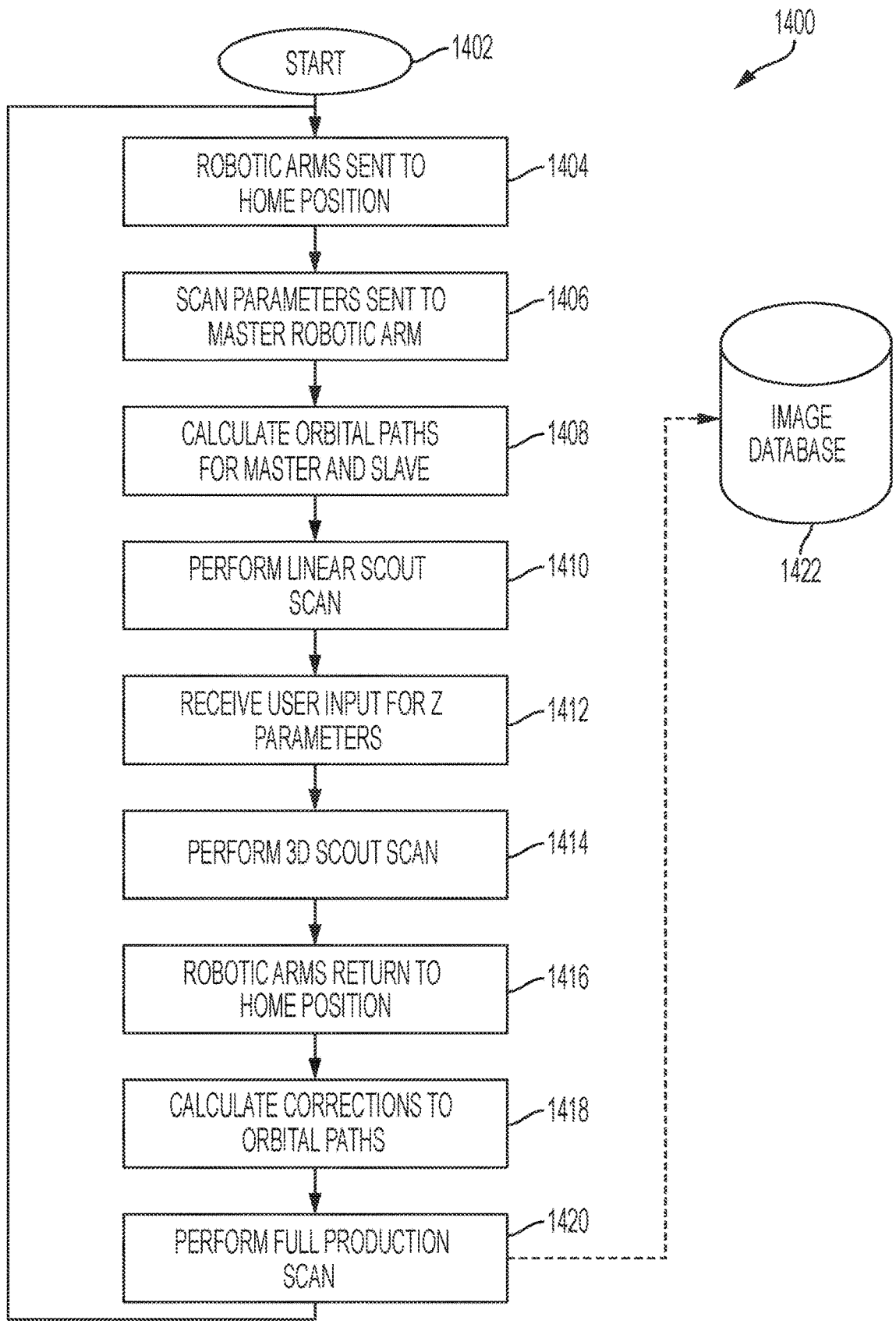
FIG. 14 depicts example operations of a CT core sample scanning system.

FIG. 14 illustrated example operations 1400 of a CT core sample scanning system. Operation commences at start block 1402 and proceeds to block 1404 where the robotic arms are sent to their home positions, for example as illustrated in FIG. 9. At block 1406, the scan parameters for the robotic arms are received by the master robotic arm. For example, a user at an associated workstation may issue a set of commands through a graphical user interface or GUI to for the robotic arms to commence scanning of one of the core samples. At block 1408, the master robotic arm calculates the trajectories for the both the master robotic arm and the slave robotic arm. At block 1410, the master robotic arm sends commands to the slave robotic arm to synchronize the operations of both robotic arms to perform a linear scout scan. The linear scout scan provides positioning information about the x, y coordinate positions of the core sample under test. At block 1412 the robotic arms can pause to allow the user to optionally provide z coordinate coverage for the 3D scout scan, and at block 1414 the master robotic arm sends commands to the slave robotic arm to synchronize the operations of both robotic arms to perform the 3D scout scan. The 3D scout scan provides information about the x, y, z and axis of rotation of the core sample under test. At block 1416 the robotic arms return to home and at block 1418 the master robotic arm calculates corrections for the position and axis of rotation of the core sample. Once the master robotic arm calculates the corrections, at block 1420 the master robotic arm sends commands to the slave robotic arm to synchronize the operations of both robotic arms to perform the full production scan. Captured images from the full production scan can be stored in a suitable data store such as database 1422 for performing the CT reconstruction. After the full production scan, processing returns to block 1404 where the robotic arms return to the home position.

The foregoing description of embodiments and examples has been presented for purposes of description. It is not intended to be exhaustive or limiting to the forms described. Numerous modifications are possible in light of the above teachings. Some of those modifications have been discussed and others will be understood by those skilled in the art. The embodiments were chosen and described for illustration of various embodiments. The scope is, of course, not limited to the examples or embodiments set forth herein but can be employed in any number of applications and equivalent articles by those of ordinary skill in the art. Rather it is hereby intended the scope be defined by the claims appended hereto.

What is claimed is:

1. A system, comprising:
   a robotic arm configured to rotate an X-ray emitter in a curvilinear path about a subject while the X-ray emitter scans the subject;
   an X-ray detector configured to capture a plurality of 2-dimensional views while the subject is scanned by the X-ray emitter; and a computed tomography reconstruction processor configured to reconstruct a digital image of the subject from the captured plurality of 2-dimensional views, wherein movement of the X-ray emitter and the X-ray detector is coordinated such that the position and angle of the X-ray emitter relative to the X-ray detector remains substantially constant while the X-ray emitter scans the subject;

wherein the robotic arm is further configured to vary the pitch of the X-ray emitter while rotating about the curvilinear path to enable the computed tomography reconstruction processor to reconstruct a high spatial resolution digital image of the subject from the captured plurality of 2-dimensional views.

2. The system of claim 1, further comprising:
a rotatable C-arm, disposed on the robotic arm, that includes the X-ray emitter and the X-ray detector.

3. The system of claim 1, further comprising:
a second robotic arm configured to independently rotate the X-ray detector about the subject in coordination with the robotic arm.

4. The system of claim 1, wherein the robotic arm is further configured to sinusoidally vary the pitch between approximately −5 degrees to approximately 5 degrees up to approximately −10 degrees to approximately 10 degrees.

5. The system of claim 1, wherein the robotic arm is further configured to move in the curvilinear path about the subject between approximately 90 degrees and 360 degrees.

6. The system of claim 1, wherein the computed tomography reconstruction processor is further configured to
generate a projection transformation matrix associated with each captured 2-dimensional view based at least in part on the movement of the robotic arm, and
apply each generated projection transformation matrix to data associated with each captured 2-dimensional view to reconstruct the digital image of the subject.

7. A system, comprising:
a robotic arm configured to rotate an X-ray emitter in a curvilinear path about a subject while the X-ray emitter scans the subject;
an X-ray detector configured to capture a plurality of 2-dimensional views while the subject is scanned by the X-ray emitter; and
a computed tomography reconstruction processor configured to reconstruct a digital image of the subject from the captured plurality of 2-dimensional views;
wherein movement of the X-ray emitter and the X-ray detector is coordinated such that the position and angle of the X-ray emitter relative to the X-ray detector remains substantially constant while the X-ray emitter scans the subject;
wherein the subject is a substantially vertical core sample suspended in a metal sleeve, and wherein the robotic arm is further configured to move the X-ray emitter about the core sample in a plane substantially perpendicular to the axis of the core sample during each scan and perform a plurality of scans of the core sample at a plurality of different heights.

8. The system of claim 7, wherein the robotic arm is further configured to selectively position the X-ray emitter about a plurality of vertically mounted core samples suspended in metal sleeves to perform a plurality of scans of each of the core samples at a plurality of different heights.

9. The system of claim 8, further comprising:
one or more rails disposed proximate to the plurality of vertically mounted core samples, wherein the robotic arm is further configured to move along the one or more rails to position the X-ray emitter proximate to each of the plurality of vertically mounted core samples during a scan.

* * * * *